United States Patent [19]
Brown et al.

[11] Patent Number: 5,342,629
[45] Date of Patent: Aug. 30, 1994

[54] PRESERVATION OF WOOD CHIPS

[75] Inventors: Roger A. Brown, Chino Hills; Richard L. Pilling; Donald C. Young, both of Fullerton, all of Calif.

[73] Assignee: Union Oil Company of California, Los Angeles, Calif.

[21] Appl. No.: 722,853

[22] Filed: Jun. 28, 1991

[51] Int. Cl.$^5$ .................... A01N 59/06; A01N 59/02
[52] U.S. Cl. .................... 424/696; 424/601; 424/682; 424/701; 424/703; 424/706; 424/707; 514/512
[58] Field of Search ............... 424/701, 703, 707, 601, 424/682, 696, 706; 558/243; 562/26; 514/512

[56] References Cited

U.S. PATENT DOCUMENTS

| | | | |
|---|---|---|---|
| 2,600,737 | 6/1952 | Crouch et al. | 558/243 |
| 2,731,487 | 1/1956 | Bashour | 558/243 |
| 2,947,111 | 8/1960 | Zobrist | 424/701 |
| 3,074,844 | 1/1963 | Ogita | 558/243 |
| 3,180,790 | 4/1965 | Goodhue | 558/243 X |
| 3,660,412 | 5/1972 | Haugwitz | 558/243 X |
| 4,078,912 | 3/1978 | Hawkins | 71/101 X |
| 4,476,113 | 10/1984 | Young et al. | 424/701 |
| 4,868,322 | 9/1989 | Degani et al. | 558/243 |
| 5,022,912 | 6/1991 | Young et al. | 424/701 |
| 5,041,240 | 8/1991 | Green, II et al. | 424/707 X |

FOREIGN PATENT DOCUMENTS 84-4230 11/1984 World Int. Prop. O. .......... 424/701

Primary Examiner—Allen J. Robinson
Assistant Examiner—John D. Pak
Attorney, Agent, or Firm—Gregory F. Wirzbicki; Charles L. Hartman

[57] ABSTRACT

Cellulosic particles, for example wood particles, stored in a pile are preserved by contacting the particles with a thiocarbonate composition.

5 Claims, No Drawings

PRESERVATION OF WOOD CHIPS

FIELD OF THE INVENTION

This invention relates to methods of preserving stored chipped wood and cellulosic materials.

STATE OF THE ART

Wood has been chipped at pulp mills for years to reduce the wood to a size that allows penetration and diffusion of the processing chemicals without excessive cutting or damage to the wood fibers. It has been found that chipped wood particles are easier to handle and store than round wood. Therefore, outdoor storage of wood particles in large piles has greatly increased in recent years. The cost of moving particles is normally less than that of round wood because wood chips, normally about 20 mm long, are fairly free flowing and can be transported pneumatically or on belts before storage in piles or bins. Consequently, logs are frequently chipped at the mill, moved to a storage site, and stored in a chip pile, now common at pulp mills. In usual practice, wood goes from being a tree to wood particles in a pile in only a few days. The wood in the pile is wet and can contain over 50% by weight water. The primary problem with wood chip piles is wood deterioration caused by biological action.

Wood particles stored for periods of time are subject to wood mass loss, the industry standard estimate being about one percent of mass lost per month stored. An industry standard time for wood particle storage time is frequently stated as being sixty days, but particles in piles at pulp mills can have residence times ranging from days to nearly a year. During this time microorganisms can attack the wood, causing the temperature of the internal portion of the wood pile to rise, and the above noted loss of wood mass as well as the loss of organic fractions such as turpentine and tall oils. The microorganisms of primary concern are divided into four general groups: a) stain and mold fungi, b) rot or decay fungi, c) soft rots, and d) yeasts and bacteria. Although each type of organism attacks different types of wood, i.e., hardwood or softwood, and at different conditions within the wood pile, world wide, these organisms seem to be the dominant causes of wood mass loss in wood particle pile. (See, for example, G. J. Hajny, Tappi, 49, 97A, (1966).) Another economically important pest for piles of pine wood chips, which is currently confined primarily to North America and Japan, is the pine wood nematode *Bursaphelenchus xylophilus* (Steiner and Buhrer). As the internal temperature of the wood pile increases, chemical oxidation of particles can become a significant source of loss. As a result, controlling the temperature rise caused by biological sources also helps to control non-biological oxidation.

Various chemicals have been tried as a chemical method of controlling wood mass loss, but most are ineffective at the amounts that can be economically used. In one study, E. L. Springer et al., Tappi, 54, 555 (1971), four different chemicals used as fungicides (sodium chlorophenolates, sodium mercaptobenzothiazole, nickel sulfate, and sodium sulfide with sodium carbonate) were tested, but none of the fungicides tested was satisfactory for preventing wood mass loss in wood particle piles.

The main problem with treating wood particle piles is that the fungicidal composition must be active for at least twenty and preferably sixty days in small enough concentrations to be economic to apply to a wood pile. Some potent and consequently less expensive fumigants known to have antifungal activity are the carbon disulfide precursors, the thiocarbonates. Thiocarbonates typically decompose rapidly into carbon disulfide. U.S. Pat. No. 4,078,912, issued to Hawkins, states that once a thiocarbonate has contacted the atmosphere it "readily" decomposes. Rapid decomposition can be tolerated for an application like soil fumigation, but the decomposition of thiocarbonates in soil would suggest that thiocarbonates would not last long enough to preserve wood piles.

A need exists for a wood particle preservative composition which can release carbon disulfide for fumigation to preserve wood particles, but which can be stored and handled safely and without significant loss of effectiveness during a reasonable commercial storage and delivery cycle.

SUMMARY OF THE INVENTION

It has now been discovered that thiocarbonates applied to wood particle piles do indeed preserve the piles for at least twenty days, and in some instances up to sixty days. The four previously listed microbial causes of wood mass loss are readily controlled, as are other pests, such as insects, including wood borers and termites. Furthermore, thiocarbonates are antioxidants providing control of temperature rise from non-biological causes as well. The chemical composition is applied to the particles. A preferred method of application is spraying a concentrated aqueous solution on the particles as the particles are piled. The preservative effect of thiocarbonates on wood particle piles can be measured by monitoring how much the internal temperature of a pile of wood increases.

Thiocarbonates, when used as wood preservative compositions, behave in an unusual manner in wood particle piles. It is apparent that the wood preservative effect of the thiocarbonates is present long after any effect would be observed in an application of the same thiocarbonate on soil. No theory or reason to explain what is causing the observed prolonged effect is presently known.

Specifically the wood preservative composition of this invention is a solid, liquid, a non-aqueous solution, or an aqueous solution containing a tri- or tetrathiocarbonate or a tri- or tetrathiocarbonate derivative selected from the group consisting of ammonium, organonitrogen cations, sulfonium cations, phosphonium cations, alkali, alkaline earth metal, transition metal, and lanthanide metal thiocarbonates; monoalkyl thiocarbonates of the form $(CS_xR^1)_yM$ where $R^1$ is selected from the group of alkyl and aryl radicals having ten carbon atoms or fewer, M is selected from the group consisting of ammonium, organonitrogen cations, sulfonium cations, phosphonium cations, alkali metals, alkaline earth metals, transition metals, and lanthanide metals, x is 3 or 4, and y is chosen to provide charge balance; and dialkyl thiocarbonates of the form $CS_xR^1R^2$ where $R^1$ and $R^2$ are independently selected from the group of alkyl and aryl radicals having ten carbon atoms or fewer and x is 3 or 4; and combinations thereof. Preferably an aqueous solution is used. It is preferably stabilized with an amount of a polysulfide selected from the group consisting of ammonium, organonitrogen cations, alkali and alkaline earth metal polysulfides of the formula $A_aS_b$, wherein A is selected from ammonium, organonitrogen cations, alkali and alkaline earth metals and combinations thereof, a and b are selected to provide charge balance, sufficient to increase the chemical stability of said thiocarbonate in said solution. It is preferred that an amount of thiocarbonate equivalent to no more than 20 pounds of carbon disulfide per oven-dried ton of wood, and more preferably equivalent to no more than 10 pounds of carbon disulfide per oven-dried ton of wood, and most preferably equivalent to no more than 5 pounds of carbon disulfide per oven-dried ton of wood be applied to the wood particles.

In the following discussion, reference will be made to the carbon disulfide content of various compositions. It should be understood that these compositions do not literally contain that amount of carbon disulfide. Rather, they contain precursor compounds that decompose to release that amount of carbon disulfide. Thus, when reference is made to a composition containing a particular amount of carbon disulfide, it is equivalent to saying that the composition is a precursor that produces that amount of carbon disulfide upon decomposition. For example, one mole of either sodium trithiocarbonate or one mole of sodium tetrathiocarbonate decomposes to produce one mole of carbon disulfide.

Wood preservative compositions described herein as "thiocarbonates," include, without limitation, salts of trithiocarbonic acid and tetrathiocarbonic acid, compositions having empirical formulae intermediate to these acid salts (such as $MCS_{3.7}$, wherein M is a divalent cation), and compositions containing substances in addition to thiocarbonates (such as a stabilized ammonium tetrathiocarbonate which contains ammonium sulfide, i.e., $(NH_4)_2CS_4\cdot(NH_4)_2S$.) Stabilized, aqueous thiocarbonate solutions useful for industrial and agricultural applications are also provided which contain an amount of added base sufficient to reduce the vapor pressure of carbon disulfide in the solution. Alternatively, the compositions can contain an amount of added sulfide and/or polysulfide sufficient to reduce the carbon disulfide vapor pressure of the solution, and compositions are also provided which contain combinations of added base and added sulfide and/or polysulfide. Thus, the stabilized aqueous thiocarbonate solutions of this invention involve aqueous solutions of thiocarbonates, soluble in the solution, and having the general formula $A_aCS_b$ wherein A is a mono- or divalent cation, b is 3 to 4, a is 2 when A is a monovalent cation, and a is 1 when A is a divalent cation, and a base and/or a sulfide and/or polysulfide of the formula $A_aS_b$, wherein A is selected from ammonium, organonitrogen cations, alkali and alkaline earth metals and combinations thereof, a and b are selected to provide charge balance. The aqueous solutions can comprise mixtures of tri- and tetrathiocarbonates having the same or different cations as well as mixtures of sulfides and polysulfides of the same or different cations.

In one aspect this invention provides a composition that includes wood particles subject to biologic deterioration of the wood together with the wood preservative composition as previously described.

In another aspect this invention provides a method for preserving wood particles by contacting a wood particle pile with the wood preservative composition described.

In a third aspect this invention also provides a method of maintaining an internal temperature in a wood pile of no more than 25° F. greater than the ambient temperature by contacting a wood particle pile with the wood preservative composition described.

The invention is directed to the fumigation of wood particles using compositions which decompose to form carbon disulfide and certain other biocidal materials. Such fumigation can be used to control primarily fungi, particularly *Ascomycetes* spp., *Fungi imperfecti*, *Trichoderma* spp., *Ceratocystis* spp., *Penicillium* spp., *Aspergillus* spp., and *Fusarium* spp., yeasts, and bacteria, as well as the pine wood nematode *Bursaphelenchus xylophilus* (Steiner and Buhrer), and secondarily insects, other nematodes, and rodents all of which are included herein in the term "pests."

DETAILED DESCRIPTION OF THE INVENTION

One commercial method of making wood chips is by mounting cutting knives on the face of a large disk that is rotated on a horizontal axis. The knives are mounted at about 35° to 40° to the axis of the fibers in the wood. As each knife severs the fibers and because of the wedge like shape of the particle, an increasing strain is placed on the cut fibers. The strain is relieved by shear along the grain. The chips tend to be remarkably uniform in size, and are usually about 10 to 30 mm, preferably about 15 to 25 mm long. This invention is usable for any fragmented and stored forest product such as chipped debarked logs, chipped logs with bark, chipped bark, or chipped whole trees.

Cellulosic particles, as the term is used herein, are any form of stored cellulosic material including wood chips, sawdust and like forms of wood: as well as non-wood sources of pulp such as papyrus, kanaf, cotton, and rags; and non-pulp cellulosic materials such as hay, silage, rice hulls, and almond hulls. Cellulosic particles as defined herein contain more than 10 wt.% water, and usually contain more than 25 wt.% water. A cellulosic particle pile as used in this disclosure and claims is an amount of cellulosic particles that experiences an internal temperature rise if untreated. As the examples appended hereto suggest, a pile so defined can comprise a modest amount of particles, perhaps as small as two or three cubic feet, although the usual size for a wood particle pile will be much larger, and all piles of wood particles larger than 15 cubic feet are included in this definition. Some wood chip piles at pulp mills are conical piles as large as one hundred feet at the base and one hundred feet high containing many thousands of tons of particles.

Fumigants for wood piles need to be continuously active since the primary pests of interest in fumigating wood particle piles are bacteria and fungi. Both of these types of pests are rapidly growing and require control throughout their life times. Stabilized, aqueous thiocarbonate solutions reduce the $CS_2$ vapor pressure, but can also be used in wood piles. This is reflected by a reduction in the $CS_2$ concentration in the equilibrium vapor phase overlying the solutions. Such compositions are particularly useful for fumigating wood particle piles. They reduce the hazards associated with $CS_2$ evolution and inhibit thiocarbonate decomposition and consequent $CS_2$ release.

The term "stability," as used herein, can be regarded as a composite of two concepts: chemical stability and physical stability. Since the effectiveness of a composition depends, at least in part, upon its ability to release carbon disulfide during decomposition, chemical stability is expressed accordingly; this can be quantified by, for example, chemically decomposing the composition and measuring the amount of carbon disulfide which evolves. Alternatively, an indication of the amount of available carbon disulfide can be obtained by spectrophotometrically determining the presence of the thiocarbonyl bond ($>C=S$) in a sample of the composition. The absorbance at wavelengths corresponding to those at which thiocarbonyl is known to absorb energy can be used for a quantitative analysis.

Symptomatic of chemical stability, but having an independent significance, is physical stability. This concept is important due to the nature of the products formed during decomposition of one of the compositions, particularly the ammonia, hydrogen sulfide, and carbon disulfide, which each have a high vapor pressure. It is readily apparent that a change in the physical form of the composition from a solution of low vapor pressure into a mixture of compounds, each possessing a high vapor pressure, imposes some rather stringent requirements upon storage containers. Vapor pressure above the composition of the invention, therefore, will be used herein as an indicator of physical stability; a condition of maintained low vapor pressure is the desired property. Another index of physical instability is the formation of undesirable insoluble precipitates, which frequently comprise sulfur, or of an immiscible liquid phase, such as carbon disulfide. The more general description of physical stability, then, is the maintenance of only a single phase in the composition.

Any amount of added base, for example, alkali metal hydroxides or oxides, alkaline earth hydroxides or oxides, ammonium hydroxide, or organonitrogen cation hydroxides, or sulfide or polysulfide, or any combination of these, enhances the solution's stability. Generally, the amount of added base, sulfide or polysulfide will correspond to about 0.01, usually about 0.02, preferably at least about 0.04, and most preferably about 0.08 moles of base, sulfide or polysulfide per mole of carbon disulfide in the solution. Concentrated, aqueous tetrathiocarbonate solutions having $CS_2$ vapor pressures corresponding to $CS_2$ concentrations in the equilibrium vapor phase below about 1 volume percent at 24° C., i.e., below the explosive limit for carbon disulfide, can be achieved with base concentrations of about 0.02 mole of base per mole of carbon disulfide. Somewhat higher base concentrations, 2 i.e., at least about 0.08 moles of base per mole of carbon disulfide, are presently preferred for producing aqueous, trithiocarbonate solutions having $CS_2$ partial pressure corresponding to about 1 volume percent or less carbon disulfide in the equilibrium vapor phase at 24° C. While significant improvements in solution stability and reductions in $CS_2$ partial pressure can be achieved by the use of sulfides and/or polysulfides in the absence of added base, the concentration of sulfide and/or polysulfide required to achieve the desired reduction in $CS_2$ partial pressure (and consequent increase in stability) is generally somewhat higher than the concentration of base required to achieve a similar stability improvement. Thus, in order to obtain a $CS_2$ partial pressure corresponding to a $CS_2$ concentration in the equilibrium vapor phase overlying the solution below 1 volume percent of 24° C., it is presently preferred to employ concentrations of sulfide and/or polysulfide of about 0.04 or more mole of sulfide and/or polysulfide per mole of carbon disulfide. As in the case of added base, greater solution stability and lower $CS_2$ partial pressures can be achieved by using even higher concentrations of sulfides and/or polysulfides, or by employing combinations of base and sulfide and/or polysulfide. Typically, the concentration of sulfide, polysulfide or combination thereof will correspond to at least about 0.02, preferably at least about 0.04, and most preferably at least about 0.08 mole of sulfide and/or polysulfide per mole of carbon disulfide. However, when combinations of base and sulfide are employed, the respective concentrations of each can be reduced by approximately ½ to obtain a comparable degree of stability improvement and $CS_2$ partial pressure reduction. In other words, the degree of stability enhancement achieved by the use of 0.02 mole of base per mole of carbon disulfide can be achieved by using approximately 0.01 mole of base in combination with about 0.01 mole of sulfide or polysulfide.

The term "organonitrogen cation" as used herein refers to a nitrogen compound of the form $NR^1R^2R^3R^4$ where each of $R^1$, $R^2$, $R^3$ and $R^4$ can be independently selected from the group consisting of hydrogen, alkyl radicals having from one to ten carbon atoms, and aryl radicals having from six to ten carbon atoms, but at least one is selected from the group consisting of alkyl radicals or aryl radicals. Examples include methyl ammonium, tetramethyl ammonium, decyl ammonium, benzyl ammonium, phenyl ammonium, trimethylbenzyl ammonium, and benzyl methyl ammonium.

The term "sulfonium cation" refers to any cation of the form $SR^1R^2R^3+$, where each of $R^1$, $R^2$, and $R^3$ can be independently selected from the group consisting of hydrogen, alkyl radicals having from one to ten carbon atoms, and aryl radicals having from six to ten carbon atoms.

The term "phosphonium cation" refers to any cation of the form $PR^1R^2R^3R^4+$, where each of $R^1$, $R^2$, $R^3$ and $R^4$ can be independently selected from the group consisting of hydrogen, alkyl radicals having from one to ten carbon atoms, and aryl radicals having from six to ten carbon atoms.

Preferred cations also include transition metal cations, such as cupric, cuprous, nickel and cobalt, and any of the lanthanide metal cations, such as gadolinium, or dysprosium.

Accordingly, the amount of base, sulfide and/or polysulfide employed should be sufficient to reduce the carbon disulfide partial pressure of the solution by the desired amount, and the amount of additive required to achieve that effect can be easily determined by adding different, known quantities of base, sulfide and/or polysulfide to the desired thiocarbonate solution, confining the vapor space over the solution at 24° C. for a sufficient period of time, e.g., about 24 hours, and analyzing the vapor phase by gas chromatography for carbon disulfide. Lower additive concentrations will result in somewhat higher $CS_2$ equilibrium concentrations (i.e., higher $CS_2$ partial pressures), and higher additive concentrations will result in lower $CS_2$ partial pressures.

The most preferred compositions, presently, are those in which the carbon disulfide partial pressure has been reduced to a level corresponding to about 1 volume percent or less carbon disulfide in the equilibrium vapor phase at 24° C. A greater safety factor, with regard to $CS_2$ partial pressure, toxicity, handling difficulty, etc., can be realized by reducing $CS_2$ partial pressure even further. Thus, more preferred thiocarbonate solutions are those in which the carbon disulfide partial pressure corresponds to less than about 0.5, most preferably less than about 0.2 volume percent carbon disulfide in the equilibrium vapor phase overlying the solution at 24° C.

The ammonium thiocarbonate compositions are stabilized by excess sulfur against significant increases in vapor pressure, and against significant solid or immiscible liquid phase formation, during reasonable storage periods, and also maintain acceptable chemical stability during such periods.

Alkaline earth metal (i.e., magnesium, calcium, strontium, and barium) thiocarbonates are somewhat more stable against loss of carbon disulfide than is an ammonium thiocarbonate. Moreover, neither alkaline earth metal nor alkali metal (lithium, sodium, potassium and cesium) thiocarbonate solutions form the phytotoxic thiocyanate species upon decomposition, so such solutions generally are more suitable for long-term storage.

Alkaline earth metal thiocarbonates can be prepared by reacting alkaline earth metal sulfides, either alone or mixed with elemental sulfur (when tetrathiocarbonate is to be prepared), with carbon disulfide, preferably in aqueous media, to directly form aqueous fumigant compositions. Alkaline earth metal sulfides can be generated in situ, by reaction of hydrogen sulfide with an aqueous solution or dispersion of alkaline earth metal salts, oxides, hydroxides, and the like. This same procedure is applicable to preparation of alkali metal thiocarbonates.

The preparation is conveniently carried out at temperatures of about 15° C. to about 35° C., but may be conducted between about 0° C. and the boiling point of carbon disulfide, preferably under an inert or reducing gas atmosphere, to avoid oxidation of sulfur compounds to sulfur oxide moieties such as thiosulfates. Reactants are preferably provided in approximately stoichiometric amounts: one mole of alkaline earth metal sulfide per mole of carbon disulfide, to form alkaline earth metal trithiocarbonate, and one molar equivalent of elemental sulfur added to form alkaline earth metal tetrathiocarbonate. Products have the empirical formula $M_nCS_x$ wherein n is 1 when M is alkaline earth metal, n is 2 when M is alkali metal, and x is 3, 4 or values between 3 and 4.

The solubility limit for alkali and alkaline earth metal trithiocarbonates in water is approximately 55 percent by weight; the limit for corresponding tetrathiocarbonates is about 45 percent by weight. Solutions are normally diluted with water to concentrations less than about 33 percent by weight, to avoid precipitation at low temperatures.

The base-containing compositions of further enhanced stability and reduced $CS_2$ partial pressure can be readily obtained by providing the desired amount of base in the thiocarbonate solution. Base can be introduced into the thiocarbonate solution before, during or after preparation of the thiocarbonate, it being necessary only that the final composition contain additional base. Preferably, such added base is provided either during or after preparation of the thiocarbonate. Similar techniques can be employed to prepare the sulfide- and polysulfide-containing compositions. Thus, the sulfide and/or polysulfide can be introduced into the thiocarbonate solution before, during or after preparation of the thiocarbonate, although such sulfides are preferably added either during or after preparation of the thiocarbonate. Sulfide and polysulfide can be provided in the composition by direct addition of such compounds, or they can be formed in situ. Thus, an amount of base, e.g., sodium hydroxide, can be added followed by addition of an equivalent quantity of hydrogen sulfide to convert the base to the corresponding sulfide, e.g., sodium sulfide ($Na_2S$). The polysulfides can be formed in situ by addition of elemental sulfur with adequate agitation to promote the reaction of the elemental sulfur with the sulfide already present in the composition. Thus, 3 mole weights of sulfur can be added to a solution containing 1 mole weight of sodium sulfide to produce a composition nominally containing sodium tetrasulfide, i.e., $Na_2S_4$. Similar preparation techniques can be employed with all ammonium, alkali and alkaline earth metal sulfides and polysulfides.

Salts may be recovered from the aqueous solutions by evaporation of the water and filtration of the resulting precipitate (under an inert or reducing atmosphere) if it is desirable to store the thiocarbonate for extremely long periods prior to use as a fumigant. However, the aqueous solution is substantially stable in and of itself; therefore, there is usually no need to recover the salt as a substantially anhydrous solid. Moreover, it is generally easier to handle the liquid solution than the solid thiocarbonate.

The above-described thiocarbonates, and in particular the aqueous, thiocarbonate solutions of enhanced stability and reduced $CS_2$ partial pressure containing added base, sulfide and/or polysulfide, can be used as fumigants for wood particles. The stabilized, concentrated compositions are particularly useful for manufacture, storage and transport of concentrated thiocarbonate compositions, particularly when it is desired to avoid the hazards associated with carbon disulfide evolution.

The above-described thiocarbonates are active fumigants and therefore may be used in any form. A powder admixed with inert solids, a solution, whether aqueous or not, or a dispersion in an organic solvent are all useful. However, one preferred embodiment is an aqueous solution used as a fumigants.

The above aqueous reaction solutions may be diluted prior to application as fumigants to provide a solution concentration of as low as 0.01 percent by weight of the thiocarbonate. The aqueous solution may incorporate surfactants to assist in application as a fumigant. Preferably, a strong base, e.g., an alkali metal hydroxide such as sodium hydroxide, is added to the aqueous solution to increase the stability thereof during application.

The compositions can be applied as fumigants in undiluted form by spraying a concentrated solution of thiocarbonate onto the wood particle pile surface, preferably followed within several hours by water application to move the composition into the wood particle pile before a significant amount of free carbon disulfide is released. An alternative method of application is dipping the wood particles in a solution of thiocarbonate before placing the particles into the pile.

Decomposition of the thiocarbonates in the diluted solutions, prior to movement into the wood particle pile, can be retarded by increasing the pH of the solutions. With waters having a high total hardness, however, even the inherent alkalinity of thiocarbonate salts can lead to the precipitation of insoluble carbonates, i.e., of calcium, which tend to plug sprinkler nozzles. Such precipitation can be retarded by the addition of a hardness-complexing agent, such as sodium hexametaphosphate, to the water.

The fumigating effectiveness of compositions described herein has been expressed primarily in terms of the available carbon disulfide content. It should be noted, however, that other components can contribute to efficacy as a fumigant. Ammonia and alkyl amines, for example, are fungicides, as is sulfur, so any of the compositions of the invention which decompose to form ammonia, alkyl amines, or sulfur will have similar properties in addition to the properties attributable to the carbon disulfide content.

Thiocarbonates are preferably directed to the control of fungi, particularly *Ascomycetes* spp., *Fungi imperfecti*, *Trichoderma* spp., *Ceratocystis* spp., *Penicillium* spp., *Aspergillus* spp.,and *Fusarium* spp., yeasts, and bacteria. These particular pests have been identified by researchers world wide as being the primary causes of wood mass losses in wood particle piles.

EXAMPLES

The invention is further described by the following examples which are illustrative of various aspects of the invention and are not intended as limiting the scope of the invention as defined by the appended claims.

Example 1

This example shows the synthesis of sodium tetrathiocarbonate.

An ammonium thiocarbonate composition was prepared, using a 12 liter, three-neck, round-bottom flask, fitted with a sealed stirrer, gas delivery tube, and a U-tube manometer. A 5461-gram charge of water was placed in the flask, and 1266 grams of anhydrous ammonia were added with cooling of the flask and stirring. With further cooling, 1266 grams of hydrogen sulfide was added. To the resulting solution was added 595 grams of finely divided sulfur and, with resumed cooling, 1412 grams of carbon disulfide was also added. Stirring was continued while the mixture was maintained at a temperature between about 24° C. and about 38° C. for a period of about one hour. The resulting clear, deep yellow solution had the following composition:

| Component | Weight Percent | Mole Percent |
|---|---|---|
| $NH_3$ | 12.66 | 16.46 |
| $H_2S$ | 12.66 | 8.22 |
| S | 5.95 | 4.11 |
| $CS_2$ | 14.12 | 4.11 |
| $H_2O$ | 54.61 | 67.1 |

This solution had a specific gravity at 21° C. of 1.130, and a crystallization temperature of about −10° C.

Example 2

This example shows the synthesis of calcium tetrathiocarbonate.

A calcium tetrathiocarbonate solution was prepared by mixing 115.8 grams of calcium oxide with 585 grams water, and adding, with vigorous stirring, 71.6 grams of hydrogen sulfide, forming a dark green slurry. When 67.4 grams of sulfur had been added, the slurry became dark yellow in color. Addition of 180.7 grams of carbon disulfide produced a deep yellow solution containing 36.5 percent by weight calcium tetrathiocarbonate.

Example 3

This example shows base-stabilized thiocarbonates.

A series of solutions containing 12.9 weight percent equivalent carbon disulfide as sodium tri- or tetrathiocarbonate were prepared by combining sodium hydroxide, deionized water, sulfur (in the case of tetrathiocarbonate only), hydrogen sulfide and carbon disulfide. In the stoichiometric solutions, the reactants were combined in proportions sufficient to provide sodium tri- or tetrathiocarbonate solutions containing 12.9 weight percent equivalent carbon disulfide without any excess reactant. In addition to the stoichiometric solutions, solutions were prepared with systematically increasing sodium hydroxide concentrations at constant equivalent carbon disulfide concentrations, so that excess base was provided in those solutions in the proportions given in the following table.

The respective solutions were prepared by combining the appropriate amounts of base, water, and elemental sulfur (when used to form the tetrathiocarbonate), in 250 ml. bottles. The contents were then weighed, and the appropriate amounts of hydrogen sulfide gas were bubbled in with cooling as necessary to form 100 grams of each of the test solutions. The bottles were then capped with Mininert valves, and the appropriate amount of carbon disulfide was added by injecting with a syringe. All sample bottles were shaken overnight to complete the reaction and were then allowed to equilibrate 3 days at 24° C., and the vapor phase was then sampled and analyzed for carbon disulfide by gas chromatography. The results are reported in the following table and show the effects of increasing base concentrations on carbon disulfide partial pressure (carbon disulfide content of the equilibrium vapor phase). Hydrogen sulfide was not detected in the vapor phase of these formulations at an $H_2S$ detection limit of 100 ppmv.

| REDUCTION OF $CS_2$ PARTIAL PRESSURE WITH BASE ADDITION | | |
|---|---|---|
| | $CS_2$ in Equilibrium Vapor at 24° C., Vol. % | |
| Base[a] | Trithiocarbonate | Tetrathiocarbonate |
| 0.00 | 27.5 | 14.4 |
| 0.02 | 34.2 | 0.87 |
| 0.04 | 30.0 | 0.47 |
| 0.08 | 0.67 | 0.29 |
| 0.12 | 0.16 | 0.27 |

[a]Equivalents of base per equivalent of $CS_2$ (1 equivalent of base is equal to 2 moles NaOH).

These results demonstrate that excess base significantly reduces the carbon disulfide vapor pressure of both tri- and tetrathiocarbonate solutions, that tetrathiocarbonate solutions have consistently lower $CS_2$ partial pressures than the corresponding trithiocarbonate solutions, and that, in the case of both the tri- and tetrathiocarbonates, the $CS_2$ partial pressure of a concentrated solution containing 12.9 weight percent mole carbon disulfide can be reduced to a level significantly below the explosive limit, i.e., nominally corresponding to 1 volume percent $CS_2$ in the equilibrium vapor phase at 4° C.

Example 4

This example shows the stabilization of thiocarbonates with sodium sulfide.

The operation described in Example 3 was repeated with the exception that sodium sulfide ($Na_2S$) was substituted for excess base. The sodium sulfide was introduced by forming solutions containing incrementally greater amounts of sodium hydroxide and then adding additional amounts of hydrogen sulfide equivalent to the amount of excess sodium hydroxide to convert the excess sodium hydroxide to sodium sulfide in situ. The results are reported in the following table:

REDUCTION OF CS$_2$ PARTIAL
PRESSURE WITH SULFIDE ADDITION

| Sulfide[a] | CS$_2$ in Equilibrium Vapor at 24° C., Vol. % | |
|---|---|---|
| | Trithiocarbonate | Tetrathiocarbonate |
| 0.00 | 27.5 | 14.4 |
| 0.02 | 45.9 | 6.60 |
| 0.04 | 1.39 | 0.74 |
| 0.08 | 0.57 | 0.12 |
| 0.12 | 0.42 | 0.13 |

[a]Equivalents of base per equivalent of CS$_2$ (1 equivalent of base is equal to 2 moles NaOH).

These results demonstrate that the carbon disulfide vapor pressure of both tri- and tetrathiocarbonate solutions can be significantly reduced by providing a sulfide in the solution, that the tetrathiocarbonate solutions have consistently lower CS$_2$ vapor pressures than the corresponding trithiocarbonate solutions, and that the CS$_2$ partial pressure of concentrated tri- and tetrathiocarbonates containing 12.9 weight percent equivalent carbon disulfide can be reduced to a level significantly below the explosive limit, i.e., below the level that would form 1 volume percent CS$_2$ in the equilibrium vapor phase at 24° C.

Example 5

This example shows stabilizing a thiocarbonate solution by making sodium sulfide in situ.

The operation described in Example 3 can be repeated using sodium tri- and tetrathiocarbonate solutions containing 12.9 weight percent equivalent carbon disulfide, 0.08 mole sodium hydroxide per mole of carbon disulfide, and 0.04 mole hydrogen sulfide per mole carbon disulfide. The thiocarbonate solutions are prepared as described in Example 4 and the amount of sodium hydroxide added in excess of that required to form the thiocarbonate corresponds to 0.08 mole sodium hydroxide per mole of carbon disulfide (keeping in mind that 2 moles of sodium hydroxide are required to react with 1 mole of hydrogen sulfide). 0.04 mole equivalent of hydrogen sulfide is then sparged into the solution, and pressure is maintained on the system with adequate mixing to assure complete reaction of the hydrogen sulfide with a portion of the excess sodium hydroxide to generate 0.04 mole equivalent of sodium sulfide (Na$_2$S). The resulting composition will have a significantly lower CS$_2$ partial pressure than an otherwise identical thiocarbonate composition in the absence of the combination of excess base and sulfide under otherwise identical conditions.

Example 6

This example demonstrates the incremental stability improvements realized by the addition of elemental sulfur, and consequent formation of polysulfides, in thiocarbonate compositions.

The half-life of an ammonium tetrathiocarbonate solution containing 32.65 weight percent ammonium tetrathiocarbonate [(NH$_4$)$_2$CS$_4$] and 12.62 weight percent mole ammonium sulfide was determined to be 14 months at 59° C. as determined by the ability of the aqueous solution to generate carbon disulfide when acidified. Thus, half of the effective carbon disulfide was still retained in the composition after storage for 14 months at 59° C.

The effect of elemental sulfur additions and the addition of free radical scavengers on the half-life of thiocarbonate solutions was determined by an accelerated aging procedure in which the compositions were stored at 84° C. in order to accelerate decomposition and thereby facilitate data acquisition. Incremental additions of 1.0, 3.0 and 5.0 weight percent elemental sulfur were made, and these correspond to 0.16, 0.48 and 0.86 moles of sulfur per mole of ammonium sulfide, respectively. Since the solutions contained 1 mole of ammonium sulfide per mole of ammonium tetrathiocarbonate (based on the weight percent values for those components given above), the amount of ammonium polysulfide in the solution corresponded, nominally, to 0.16, 0.48 and 0.86 moles polysulfide per mole of thiocarbonate for the 3 sulfur concentrations employed. The results are presented in the following table:

EFFECT OF VARIOUS
ADDITIVES ON THIOCARBONATE HALF-LIFE

| Additive | Concentration Wt. % | Increase (Decrease) Half-Life, % |
|---|---|---|
| Hydroquinone | 0.5 | 0 |
| | 1.0 | (5) |
| | 2.0 | (13) |
| p-Methoxyphenol | 0.5 | 0 |
| | 1.0 | 0 |
| | 2.0 | 0 |
| Citric Acid, Na Salt | 0.5 | 0 |
| | 1.0 | 0 |
| | 2.0 | 0 |
| Ascorbic Acid | 0.5 | 0 |
| | 1.0 | 0 |
| | 2.0 | 0 |
| Elemental Sulfur | 1.0 | 0 |
| | 3.0 | 16 |
| | 5.0 | 22 |
| Triethylamine | 1.0 | 0 |
| | 3.0 | (18) |
| | 5.0 | (22) |
| Urea | 5.0 | 0 |
| | 10.0 | (7) |
| | 20.00 | (13) |

These results demonstrate that small incremental additions of sulfur produce significant incremental additions in the thiocarbonate half-life, since only 5 weight percent elemental sulfur increased thiocarbonate half-life by 22 percent, whereas the remaining additives, the free radical scavengers, either had no effect or a negative effect on solution stability.

Examples 7–14

This series of Examples shows using thiocarbonate solutions to preserve a mass of moist wood chips.

Slash pine logs, cut from the forest in Sumpter County, Georgia were shipped to the United States Department of Agriculture, Forest Products Laboratory in Madison, Wis. Logs were randomly selected, debarked and chipped into 15 mm particles about three weeks after harvest. Some of the particles were retained as a control and were not treated in any way (Example 7). The remaining chips were divided between fourteen nylon mesh bags. Pairs of the bags, each pair of bags representing one Example, were immersed for fifteen seconds in 150 pounds of the appropriate treating solution as defined in Table A, which was contained in a 30 gallon plastic garbage can. After treatment the bagged particles were allowed to drain for 2 hours. The particles were then removed from the bags and most of the particles from each pair of bags were loaded into an insulated box having a 4 cubic foot capacity. The boxes were made from polystyrene foam 2.5 inch thick and fitted with a manifold to allow water-saturated air to flow continuously throughout the particle mass. Samples of the particles were taken to be analyzed for moisture and pH determinations. The amount of solution takeup and pH before and after the sixty day test period is given in Table B.

TABLE A

SOLUTIONS USED FOR TREATING SLASH PINE CHIPS

| Example | Stock solution* | Amount of stock solution, g | Amount of water, lb. | NaOH, g | Treating Solution Composition, wt. % | |
|---|---|---|---|---|---|---|
| 8 | A | 2800 | 143.8 | 0 | $Na_2CS_4$ | −1.42 |
|   |   |      |       |   | $Na_2S$    | −0.030 |
| 9 | A | 700  | 148.5 | 0 | $Na_2CS_4$ | −0.36 |
|   |   |      |       |   | $Na_2S$    | −0.008 |
| 10 | A | 700 | 148.1 | 150 | $Na_2CS$ | −0.36 |
|    |   |     |       |     | $Na_2S$  | −0.008 |
|    |   |     |       |     | NaOH     | −0.22 |
| 11 | B | 2800 | 143.8 | 0 | $(NH_4)_2CS_4$ | −1.30 |
|    |   |      |       |   | $(NH_4)_2S$    | −0.50 |
| 12 | B | 960  | 147.9 | 0 | $(NH_4)_2CS_4$ | −0.45 |
|    |   |      |       |   | $(NH_4)_2S$    | −0.17 |
| 13 | C | 2800 | 143.8 | 0 | $Na_2CS_4$ | −1.42 |
|    |   |      |       |   | $Na_2S$    | −0.44 |
| 14 | C | 1400 | 146.9 | 0 | $Na_2CS_4$ | −0.71 |
|    |   |      |       |   | $Na_2S$    | −0.22 |

*Stock solution A = $Na_2CS_4$ (14.12% $CS_2$) + $Na_2S$, 1:0.05 (mole:mole)
Stock solution B = $(NH_4)_2CS_4$ (13.69% $CS_2$) + $(NH_4)_2S$, 1:1 (mole:mole)
Stock solution C = $Na_2CS_4$ (14.09% $CS_2$) + $Na_2S$, 1:0.73 (mole:mole)

TABLE B

CHEMICAL PICKUP AND PH OF TREATED AND UNTREATED CHIPS

| Example | Weight of chips in box, lb. | Moisture of chips in box, % | Solution pickup of box chips, lb. | Chemical pickup pounds $CS_2$ per o.d. tons of chips | Chip pH Initial | Chip pH Final |
|---|---|---|---|---|---|---|
| 7  | 93  | 42 | —    | —    | 5.0 | 5.2 |
| 8  | 108 | 51 | 15.2 | 3.3  | 7.5 | 5.3 |
| 9  | 99  | 48 | 11.1 | 0.61 | 6.3 | 5.2 |
| 10 | 108 | 48 | 14.7 | 0.78 | 6.1 | 6.2 |
| 11 | 103 | 53 | 12.3 | 2.8  | 8.4 | 4.9 |
| 12 | 99  | 53 | 11.8 | 0.99 | 8.2 | 4.8 |
| 13 | 104 | 52 | 14.0 | 3.2  | 7.6 | 6.6 |
| 14 | 119 | 50 | 15.9 | 1.6  | 7.4 | 6.0 |

TABLE C

DEGREES FAHRENHEIT ABOVE AMBIENT TEMPERATURE

| Day Number | Example 7 | 8 | 9 | 10 | 11 | 12 | 13 | 14 |
|---|---|---|---|---|---|---|---|---|
| 5  | 15 | 6  | 11 | 7  | 5  | 16 | 3  | 6  |
| 10 | 20 | 7  | 16 | 18 | 5  | 21 | 5  | 10 |
| 15 | 15 | 3  | 13 | 12 | 11 | 22 | 10 | 11 |
| 20 | 15 | 10 | 13 | 13 | 30 | 33 | 18 | 12 |
| 25 | 17 | 20 | 17 | 15 | 30 | 35 | 15 | 12 |
| 30 | 16 | 22 | 18 | 15 | 31 | 31 | 14 | 13 |
| 35 | 7  | 10 | 7  | 5  | 17 | 17 | 4  | 4  |
| 40 | 8  | 9  | 7  | 5  | 11 | 13 | 4  | 5  |
| 45 | 6  | 8  | 5  | 3  | 9  | 12 | 3  | 5  |
| 50 | 7  | 9  | 8  | 4  | 7  | 11 | 3  | 5  |
| 55 | 3  | 6  | 4  | 2  | 5  | 8  | 1  | 2  |
| 60 | 6  | 9  | 7  | 6  | 8  | 12 | 4  | 6  |

After filling, the boxes were attached to a water-saturated air supply and 1.4 cubic feet of moist air was metered through each box every day. A copper-constantan thermocouple was placed at the geometric center of each box to monitor heat evolved during storage. The temperature, reported as degrees Fahrenheit above ambient temperature, is given in Table C. Example 8 provided the best temperature control initially, but it gave poor results after day twenty. Example 14 gave the most consistently good results with the temperature never exceeding 12 degrees above ambient temperature for sixty days. Example 11 gave superior results for 14 days, but then exhibited a sharp temperature rise.

The pH of chip samples was determined by placing a few chips in a hydraulic press. A liquor sample was squeezed from the chips and the pH of the liquor was determined using a glass electrode. The results are tabulated in Table B.

Surprisingly, all the thiocarbonate solutions except Examples 9 and 12 showed at least some temperature rise inhibitory effect for at least the first ten to fifteen days. Examples 8 and 9 used a non-stabilized form of thiocarbonate solution. Examples 11 and 12 used a form of ammonium thiocarbonate. Examples 10, 13 and 14 used stabilized forms of thiocarbonate. But all forms of thiocarbonate used showed activity for at least the first ten days of the experiment, far longer than would have been predicted on the basis of thiocarbonate soil stability. Example 14 showed good temperature control for the duration of the test.

Although this invention has been primarily described in conjunction with examples and by references to embodiments thereof, it is evident that the foregoing description will suggest many alternatives, modifications, and variations to those skilled in the art. Accordingly, the spirit and scope of the appended claims are intended to embrace within the invention all such alternatives, modifications, and variations.

What is claimed is:

1. A method of preserving cellulosic particles comprising:
    forming a solution of a thiocarbonate selected from the group consisting of alkali metal and alkaline earth metal trithiocarbonate and tetrathiocarbonate, and combinations thereof, wherein said solution contains a sulfide that is soluble in said solution and that has the formula $A_aS_b$ wherein A is selected from the group consisting of sulfonium cation, phosphonium cation, alkali metal and alkaline earth metal, and a and b are selected to provide charge balance, and combinations thereof, the concentration of said sulfide being sufficient to increase the stability of said thiocarbonate in said solution; and applying a sufficient amount of the solution to a volume comprising at least three cubic feet of cellulosic particles to prevent a temperature rise within the volume of the cellulosic particles of more than 25° F. for at least 20 days.

2. The method of claim 1 further comprising providing in said solution a base selected from the group consisting of alkali metal and alkaline earth metal hydroxides or oxides, and combinations thereof, and sufficient sulfur and hydrogen sulfide to convert at least a portion of said base to said sulfide.

3. The method of claim 1 wherein the thiocarbonate solution contains at least about 0.02 mole of said sulfide per mole of carbon disulfide, wherein the amount of carbon disulfide is calculated as the amount of carbon disulfide that would be released by said thiocarbonate upon decomposition.

4. The method of claim 1 wherein in the applying step an amount of thiocarbonate equal to not more than 20 pounds of carbon disulfide per oven-dried ton of cellulosic particles is applied to the cellulosic particles, wherein the amount of carbon disulfide is calculated as the amount of carbon disulfide that would be released by said thiocarbonate upon decomposition.

5. The method defined in claim 1, wherein said thiocarbonate comprises a member selected from the group consisting of sodium, potassium and calcium thiocarbonates, and combinations thereof, and the concentration of said thiocarbonate corresponds to at least about 10 weight percent carbon disulfide, wherein the amount of carbon disulfide is calculated as the amount of carbon disulfide that would be released by said thiocarbonate upon decomposition.

* * * * *